(12) United States Patent
Yi et al.

(10) Patent No.: US 12,136,700 B2
(45) Date of Patent: *Nov. 5, 2024

(54) LITHIUM-ION BATTERY AND APPARATUS

(71) Applicant: CONTEMPORARY AMPEREX TECHNOLOGY (HONG KONG) LIMITED, Hong Kong (CN)

(72) Inventors: Tiancheng Yi, Ningde (CN); Chunhua Hu, Ningde (CN); Yao Jiang, Ningde (CN); Shushi Dou, Ningde (CN); Chengdu Liang, Ningde (CN)

(73) Assignee: CONTEMPORARY AMPEREX TECHNOLOGY (HONG KONG) LIMITED, Hong Kong (CN)

( * ) Notice: Subject to any disclaimer, the term of this patent is extended or adjusted under 35 U.S.C. 154(b) by 232 days.

This patent is subject to a terminal disclaimer.

(21) Appl. No.: 17/697,265

(22) Filed: Mar. 17, 2022

(65) Prior Publication Data

US 2022/0209296 A1 Jun. 30, 2022

Related U.S. Application Data

(63) Continuation of application No. 17/128,581, filed on Dec. 21, 2020, now Pat. No. 11,316,197, which is a continuation of application No. PCT/CN2019/125313, filed on Dec. 13, 2019.

(30) Foreign Application Priority Data

Dec. 14, 2018 (CN) .......................... 201811535393.0

(51) Int. Cl.
| | | |
|---|---|---|
| H01M 10/0567 | (2010.01) | |
| C07D 239/04 | (2006.01) | |
| C07D 241/04 | (2006.01) | |
| C07D 251/04 | (2006.01) | |
| C07D 295/15 | (2006.01) | |
| C07D 403/04 | (2006.01) | |
| H01M 4/525 | (2010.01) | |
| H01M 10/0525 | (2010.01) | |
| H01M 10/0569 | (2010.01) | |
| H01M 10/42 | (2006.01) | |
| H01M 4/02 | (2006.01) | |

(52) U.S. Cl.
CPC ...... *H01M 10/0567* (2013.01); *C07D 239/04* (2013.01); *C07D 241/04* (2013.01); *C07D 251/04* (2013.01); *C07D 295/15* (2013.01); *C07D 403/04* (2013.01); *H01M 4/525* (2013.01); *H01M 10/0525* (2013.01); *H01M 10/0569* (2013.01); *H01M 10/4235* (2013.01); *H01M 2004/028* (2013.01); *H01M 2300/0025* (2013.01); *H01M 2300/004* (2013.01)

(58) Field of Classification Search
None
See application file for complete search history.

(56) References Cited

U.S. PATENT DOCUMENTS

| | | | |
|---|---|---|---|
| 9,819,054 B2 | 11/2017 | Kang et al. | |
| 10,388,990 B2 | 8/2019 | Kang et al. | |
| 11,177,508 B2 * | 11/2021 | Jiang ................ | H01M 10/0567 |
| 11,695,157 B2 * | 7/2023 | Yi ..................... | H01M 10/0567 429/200 |
| 2004/0142240 A1 | 7/2004 | Nagayama et al. | |
| 2005/0042519 A1 | 2/2005 | Roh et al. | |
| 2010/0035146 A1 | 2/2010 | Fujii et al. | |
| 2012/0231330 A1 | 9/2012 | Fujii et al. | |
| 2013/0337318 A1 | 12/2013 | Fujii et al. | |
| 2015/0064578 A1 | 3/2015 | Kang et al. | |
| 2015/0162644 A1 | 6/2015 | Fujii et al. | |
| 2017/0040639 A1 | 2/2017 | Wang et al. | |
| 2018/0013168 A1 | 1/2018 | Yu et al. | |
| 2018/0026306 A1 | 1/2018 | Kang et al. | |
| 2018/0183104 A1 | 6/2018 | Fujii et al. | |
| 2019/0326634 A1 | 10/2019 | Yi et al. | |
| 2019/0326641 A1 | 10/2019 | Dou et al. | |

FOREIGN PATENT DOCUMENTS

| | | |
|---|---|---|
| CN | 103078140 B | 4/2015 |
| CN | 103618081 B | 4/2015 |
| CN | 103022556 B | 6/2015 |
| CN | 105098244 A | 11/2015 |

(Continued)

OTHER PUBLICATIONS

Extended European Search Report for Application No. 19896480.1, mailed on Aug. 30, 2021, 12 pages.
International Search Report for Application No. PCT/CN2019/125313, mailed on Mar. 16, 2020, 4 pages.
Written Opinion for Application No. PCT/CN2019/125313, mailed on Mar. 16, 2020, 6 pages.

*Primary Examiner* — Laura Weiner

(74) *Attorney, Agent, or Firm* — Ladas & Parry LLP

(57) ABSTRACT

The present application provides a lithium-ion battery and an apparatus, and the lithium-ion battery includes an electrode assembly and an electrolytic solution, the electrode assembly includes a positive electrode sheet, a negative electrode sheet and a separation film. A positive active material of the positive electrode sheet includes $Li_{x1}Co_{y1}M_{1-y1}O_{2-z1}Q_{z1}$, $0.5 \leq x1 \leq 1.2$, $0.85 \leq y1 \leq 1.0$, $0 \leq z1 \leq 0.1$ M is selected from one or more of Al, Ti, Zr, Y, and Mg, and Q is selected from one or more of F, Cl, and S. The electrolytic solution contains vinylene carbonate, fluoroethylene carbonate, 1,3-propane sultone, and an additive A. The additive A is a polynitrile six-membered nitrogen-heterocyclic compound with a relatively low oxidation potential. The lithium-ion battery has superb cycle performance and storage performance, especially under high-temperature and high-voltage conditions.

6 Claims, 4 Drawing Sheets

(56) References Cited

FOREIGN PATENT DOCUMENTS

| | | | |
|---|---|---|---|
| CN | 105633460 | A | 6/2016 |
| CN | 105789684 | A | 7/2016 |
| CN | 106356561 | A | 1/2017 |
| CN | 110391461 | A | 4/2018 |
| CN | 110391460 | A | 10/2019 |
| EP | 2120279 | A1 | 11/2009 |
| EP | 3279998 | A1 | 2/2018 |
| JP | 11111332 | A | 4/1999 |
| JP | 4815660 | B2 | 11/2011 |

* cited by examiner

LITHIUM-ION BATTERY AND APPARATUS

CROSS-REFERENCE TO RELATED APPLICATIONS

The present application is a Divisional of Ser. No. 17/128,581 filed Dec. 21, 2020 which is a continuation of International Application No. PCT/CN2019/125313, filed on Dec. 13, 2019 now U.S. Pat. No. 11,316,197, which claims priority to Chinese Patent Application No. 201811535393.0, filed on Dec. 14, 2018. Both of the aforementioned applications are hereby incorporated by reference in their entireties.

TECHNICAL FIELD

The present application relates to the field of energy storage materials, and in particular, to a lithium-ion battery and an apparatus.

BACKGROUND

Lithium-ion batteries are widely applied to electromobiles and consumer electronic products due to their advantages such as high energy density, high output power, long cycle life, and low environmental pollution. Current requirements on lithium-ion batteries are high voltage, high power, long cycle life, long storage life, and superb safety performance.

Currently, $LiCoO_2$ is widely used as a positive active material in lithium-ion batteries and shows relatively stable performance during cycling between fully discharged $LiCoO_2$ and semi-charged $Li_{0.5}CoO_2$ (4.2 V vs. Li). Therefore, lithium ions that are actually used account only for ½ of lithium ions actually contained in $LiCoO_2$. When the voltage is greater than 4.2 V, the remaining ½ of lithium ions contained in $LiCoO_2$ may continue to be extracted. However, during deep delithiation, $Co^{3+}$ is oxidized into quite unstable $Co^{4+}$, which oxidizes an electrolytic solution together with surface oxygen that loses a large quantity of electrons. In this case, a large amount of gas is produced inside the batteries, causing the batteries to swell. In addition, due to a corrosive effect of HF in the electrolytic solution on a surface of a positive electrode, $Co^{4+}$ is dissolved in the electrolytic solution and deposited on a surface of a negative electrode, catalyzing reduction of the electrolytic solution, and also producing a large amount of gas that causes the batteries to swell. In addition, due to high overlapping between a 3d energy level of Co and a 2p energy level of O, the deep delithiation also causes lattice oxygen to lose a large quantity of electrons, resulting in sharp shrinkage of $LiCoO_2$ unit cells along a c-axis direction, and leading to instability or even collapse of a local bulk structure. This eventually causes loss of $LiCoO_2$ active sites, and a rapid decrease in capacity of the lithium-ion batteries. Therefore, $LiCoO_2$ has very poor performance when being used in a high-voltage system greater than 4.2 V.

In view of this, the application is hereby proposed.

SUMMARY

In view of the problems in the background, an objective of the present application is to provide a lithium-ion battery and an apparatus. The lithium-ion battery has superb cycle performance and storage performance, especially under high-temperature and high-voltage conditions.

To achieve the foregoing objective, according to a first aspect, the present application provides a lithium-ion battery, including an electrode assembly and an electrolytic solution, wherein the electrode assembly includes a positive electrode sheet, a negative electrode sheet, and a separation film. A positive active material of the positive electrode sheet includes $Li_{x1}Co_{y1}M_{1-y1}O_{2-z1}Q_{z1}$, where $0.5 \le x1 \le 1.2$, $0.8 \le y1 \le 1.0$, $0 \le z1 \le 0.1$, M is selected from one or more of Al, Ti, Zr, Y, and Mg, and Q is selected from one or more of F, Cl, and S. The electrolytic solution contains vinylene carbonate, fluoroethylene carbonate, 1,3-propane sultone, and an additive A. The additive A is selected from one or more of compounds represented by Formula I-1, Formula I-2, and Formula I-3. In the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group is selected from one or more of a halogen atom, a nitrile group, a $C_1$-$C_6$ alkyl group, a $C_2$-$C_6$ alkenyl group, and a $C_1$-$C_6$ alkoxy group; x, y, and z each are independently selected from integers 0-8; and m, n, and k each are independently selected from integers 0-2.

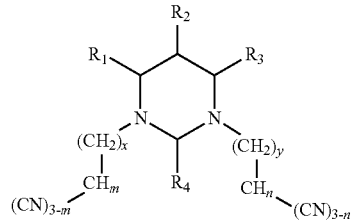

Formula I-1

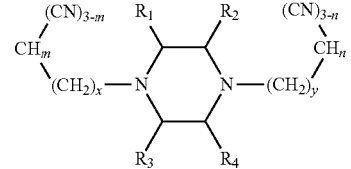

Formula I-2

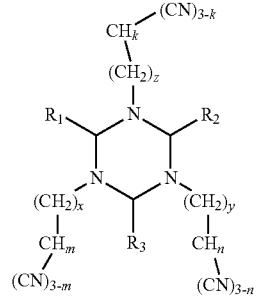

Formula I-3

According to a second aspect of the present application, the present application provides an apparatus, including the lithium-ion battery as described in the first aspect of the present application.

Compared with the prior art, the present application provides at least the following beneficial effects: in the present application, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material.

This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V. The electrolytic solution used in the present application also contains a polynitrile six-membered nitrogen-heterocyclic compound with a relatively low oxidation potential, such that a stable complex layer can be formed on a surface of the positive active material during formation of the battery. This could effectively passivate the surface of the positive active material, reduce surface activity of the positive active material, and suppress dissolution of a transition metal (especially cobalt) into the electrolytic solution, thereby reducing gas production of the battery while reducing side reactions. The electrolytic solution of the present application further contains VC, FEC, and PS. These additives may form, on surfaces of positive and negative electrodes, a surface film containing double bonds, fluorine atoms, and sulfonate groups. The surface film has good chemical, electrochemical, mechanical, and thermal stability, and can avoid direct contact between the electrolytic solution and the surfaces of the positive and negative electrodes while smoothly conducting lithium ions, thereby providing an effect of suppressing oxidation and reduction side reactions on the surfaces of the positive and negative electrodes, especially significantly suppressing gas production of the battery. Therefore, the lithium-ion battery of the present application has superb cycle performance and storage performance, especially under high-temperature and high-voltage conditions. The apparatus of the present application includes the lithium-ion battery as described in the first aspect of the present application, and therefore provides at least the same advantages as the lithium-ion battery.

DETAILED DESCRIPTION OF EMBODIMENTS

Figure 1:
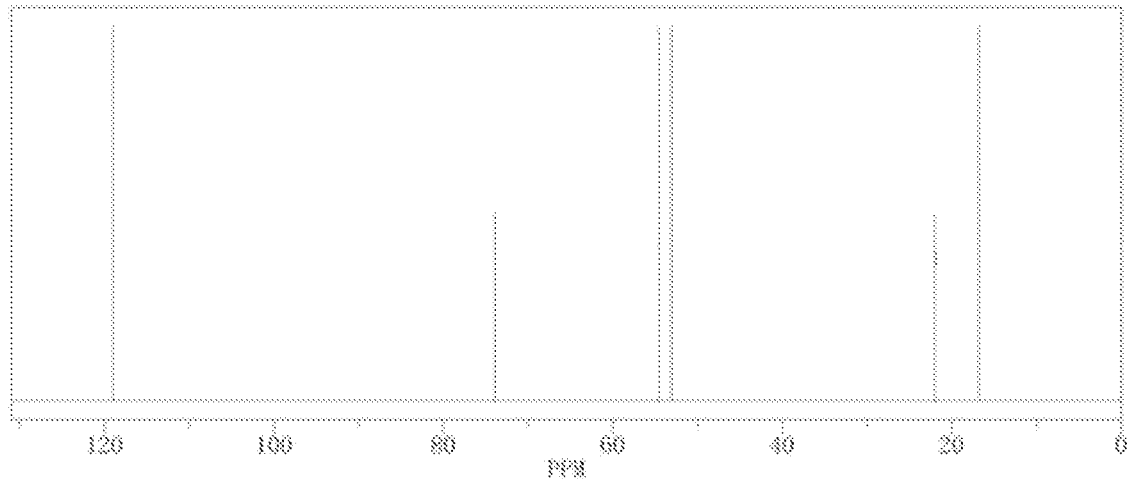
FIG. 1 is a carbon nuclear magnetic resonance spectrum of a compound A1.

The following describes in detail the lithium-ion battery and apparatus according to the present application.

A lithium-ion battery according to a first aspect of the present application is described first.

The lithium-ion battery according to the present application includes an electrode assembly and an electrolytic solution. The electrode assembly includes a positive electrode sheet, a negative electrode sheet, and a separation film. A positive active material of the positive electrode sheet includes $Li_{x1}Co_{y1}M_{1-y1}O_{2-z1}Q_{z1}$, where $0.5 \leq x1 \leq 1.2$, $0.8 \leq y1 \leq 1.0$, $0 \leq z1 \leq 0.1$, M is selected from one or more of Al, Ti, Zr, Y, and Mg, and Q is selected from one or more of F, Cl, and S. The electrolytic solution contains vinylene carbonate (VC), fluoroethylene carbonate (FEC), 1,3-propane sultone (PS), and an additive A. The additive A is selected from one or more of compounds represented by Formula I-1, Formula I-2, and Formula I-3.

In the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group (indicating a substitution case in the "substituted or unsubstituted" mentioned in the present application) is selected from one or more of a halogen atom, a nitrile group, a $C_1$-$C_6$ alkyl group, a $C_2$-$C_6$ alkenyl group, and a $C_1$-$C_6$ alkoxy group; x, y, and z each are independently selected from integers 0-8; and m, n, and k each are independently selected from integers 0-2.

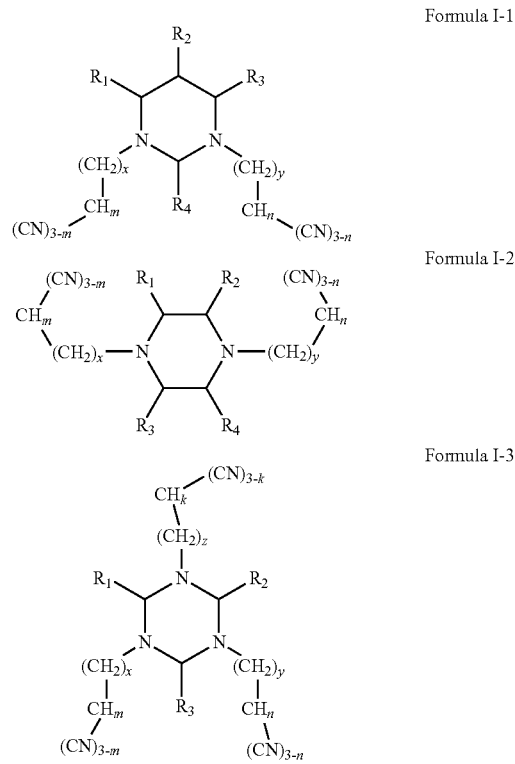

Formula I-1

Formula I-2

Formula I-3

The lithium-ion battery of the present application has superb cycle performance and storage performance, especially under high-temperature and high-voltage conditions. Details are as follows:

(1) In the present application, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material. This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V.

(2) The additive A contained in the electrolytic solution in the present application is a polynitrile six-membered nitrogen-heterocyclic compound with a relatively low oxidation potential. Nitrogen atoms in the nitrile groups contain lone pair electrons, which have relatively strong complexation with a transition metal in the positive active material. After being applied in the electrolytic solution, the additive A may be adsorbed on a surface of the positive active material during formation of the battery to form a loose and porous complex layer and effectively passivate the surface of the positive active material. The complex layer could avoid direct contact between the surface of the positive active material and the electrolytic solution and reduce surface activity of the positive active material, and could further reduce a large quantity of side reactions on the surface of the positive active material and suppress dissolution of a transition metal (especially cobalt) into the electrolytic solution. Therefore, the electrolytic solution in the present application may have an effect of reducing side reaction products and reducing gas production.

(3) The additive A in the present application has a special six-membered nitrogen-heterocyclic structure. A spacing between nitrile groups is closer to that between transition metals on the surface of the positive active material. This could maximize complexation of the nitrile groups and allow more nitrile groups to have a complexation effect. Therefore, compared with a conventional linear nitrile compound, the polynitrile six-membered nitrogen-heterocyclic compound in the present application has a better passivation effect.

(4) The special six-membered nitrogen-heterocyclic structure of the additive A in the present application can further lower an oxidation potential of molecules, so that a stable complex layer may be formed on the surface of the positive active material during formation of the battery. This may help improve electrochemical performance of an entire battery system, for example, by reducing gas production and extending a cycle life under high-temperature and high-voltage conditions.

(5) The electrolytic solution of the present application further contains VC, FEC, and PS. These additives may form, on surfaces of positive and negative electrodes, a surface film containing double bonds, fluorine atoms, and sulfonate groups. The surface film has good chemical, electrochemical, mechanical, and thermal stability, and can avoid direct contact between the electrolytic solution and the surfaces of the positive and negative electrodes while smoothly conducting lithium ions, thereby providing an effect of suppressing oxidative and reductive side reactions on the surface of the positive and negative electrodes. Therefore, the gas production of the battery could be significantly suppressed, and the cycle performance and storage performance of a high-voltage lithium-ion battery system could be improved.

In the lithium-ion battery of the present application, preferably, based on total mass of the electrolytic solution, a mass percentage of the additive A is 0.1%-10%. If the amount of the additive A is too low, improvement made by the additive A to the electrolytic solution is not obvious; if the amount of the additive A is too high, the complex layer formed by the additive A being adsorbed on the surface of the positive active material would be too thick and dense, affecting diffusion and migration of lithium ions, and greatly increasing positive electrode impedance. In addition, excessively high amount of the additive A further causes an increase in overall viscosity of the electrolytic solution and a decrease in an ionic conductivity, and therefore, affects performance of the lithium-ion battery. Preferably, an upper limit of the amount of the additive A may be any one selected from 10%, 9%, 8%, 7%, 6%, 5%, 4.5%, 4%, 3.5%, 3%, 2.5%, 2%, 1.5%, 1%, or 0.8%, and a lower limit of the amount of the additive A may be any one selected from 0.1%, 0.2%, 0.3%, 0.4%, 0.5%, 0.6%, 0.7%, 0.8%, 0.9%, 1.0%, or 1.2%.

Further preferably, the mass percentage of the additive A is 0.1%~6% based on the total mass of the electrolytic solution. More preferably, the mass percentage of the additive A is 0.1~3.5% based on the total mass of the electrolytic solution.

In the lithium-ion battery of the present application, preferably, based on the total mass of the electrolytic solution, mass percentageages of vinylene carbonate, fluoroethylene carbonate, and 1,3-propane sultone are 0.1%-10%, respectively. Further preferably, based on the total mass of the electrolytic solution, the mass percentageages of vinylene carbonate, fluoroethylene carbonate, and 1,3-propane sultone are 0.1%-5%, respectively.

In the lithium-ion battery of the present application, the electrolytic solution further includes an organic solvent and an electrolyte salt.

The organic solvent used in the electrolytic solution in an embodiment of the present application may include a cyclic carbonate and a chain carbonate, and could further improve cycle performance and storage performance of the lithium-ion battery under high-temperature and high-voltage conditions. In addition, it is easy to adjust a conductivity of the electrolytic solution to a suitable range, thus further helping the additives achieve a better film-forming effect.

The organic solvent used in the electrolytic solution in an embodiment of the present application may further include a carboxylic acid ester. To be specific, the organic solvent in the present application may include a mixture of a cyclic carbonate, a chain carbonate, and a carboxylic acid ester. The carboxylic acid ester is characterized by large dielectric constant and low viscosity, and could effectively prevent association of lithium ions and anions in the electrolytic solution. In addition, the carboxylic acid ester is more advantageous than the cyclic carbonate and the chain carbonate in terms of ion conduction. Especially at low temperature, the carboxylic acid ester could ensure good ion conduction for the electrolytic solution.

Based on total mass of the organic solvent, a mass percentage of the cyclic carbonate may be 15%-55%, preferably 25%-50%; a mass percentage of the chain carbonate may be 15%-74%, preferably, 25%-70%; and a mass percentage of the carboxylic acid ester may be 0.1%-70%, preferably, 5%-50%.

Specifically, the cyclic carbonate may be selected from one or more of an ethylene carbonate, a propylene carbonate, a 1,2-butylene carbonate, and a 2,3-butanediol carbonate. More preferably, the cyclic carbonate may be selected from one or more of an ethylene carbonate and a propylene carbonate.

Specifically, the chain carbonate may be one or more asymmetric chain carbonates selected from an ethyl methyl carbonate, a methyl propyl carbonate, a methyl isopropyl carbonate, a methyl butyl carbonate, and an ethyl propyl carbonate; the chain carbonate may also be one or more symmetric chain carbonates selected from a dimethyl carbonate, a diethyl carbonate, a dipropyl carbonate, and a dibutyl carbonate; the chain carbonate may also be a mixture of the asymmetric chain carbonate and the symmetric chain carbonate.

Specifically, the carboxylic acid ester may be selected from one or more of methyl pivalate, ethyl pivalate, propyl pivalate, butyl pivalate, methyl butyrate, ethyl butyrate, propyl butyrate, butyl butyrate, methyl propionate, ethyl propionate, propyl propionate, butyl propionate, methyl acetate, ethyl acetate, propyl acetate, and butyl acetate.

The electrolyte salt used in the present application may suitable include the following lithium salts.

(Li salt-Class 1): It is suitable to include a "complex salt of a Lewis acid and LiF" selected from one or more of $LiPF_6$, $LiBF_4$, $LiAsF_6$, $LiSbF_6$, $LiPF_4(CF_3)_2$, $LiPF_3(C_2F_5)_3$, $LiPF_3(CF_3)_3$, $LiPF_3(iso-C_3F_7)_3$, and $LiPF_5(iso-C_3F_7)$, preferably selected from $LiPF_6$, $LiBF_4$, and $LiAsF_6$, and more preferably selected from $LiPF_6$, and $LiBF_4$.

(Li salt-Class 2): it is suitable to include a "imidized or methylated lithium salt" selected from one or more of $(CF_2)_2(SO_2)_2NLi$ (cyclic), $(CF_2)_3(SO_2)_2NLi$ (cyclic), and $LiC(SO_2CF_3)_3$.

(Li salt-Class 3): it is suitable to include a "lithium salt including a structure of $S(=O)_2O$" selected from one or more of $LiSO_3F$, $LiCF_3SO_3$, $CH_3SO_4Li$, $C_2H_5SO_4Li$, $C_3H_7SO_4Li$, lithium trifluoro((methylsulfonyl)oxy) borate (LiTFMSB), lithium pentafluoro((methylsulfonyl)oxy) phosphate (LiPFMSP), and more preferably selected from $LiSO_3F$, $CH_3SO_4Li$, $C_2H_5SO_4Li$ or LiTFMSB.

(Li salt-Class 4): it is suitable to include a "lithium salt including a structure of P=O or Cl=O" selected from one or more of $LiPO_2F_2$, $Li_2PO_3F$, and $LiClO_4$, and preferably selected from $LiPO_2F_2$, $Li_2PO_3F$.

(Li salt-Class 5): it is suitable to include a "lithium salt with oxalate ligands as positive ions" selected from one or more of lithium bis[oxalate-O,O'] borate (LiBOB), lithium difluoro[oxalate-O,O'] borate, lithium difluorobis[oxalate-O,O'] phosphate (LiPFO), and lithium tetrafluoro[oxalate-O,O']phosphate, and more preferably selected from LiBOB and LiPFO.

The above lithium salts may be used individually or in combination. Preferably, the lithium salt is selected from one or more of $LiPF_6$, $LiPO_2F_2$, $Li_2PO_3F$, $LiBF_4$, $LiSO_3F$, lithium trifluoro((methylsulfonyl)oxy) borate (LiTFMSB), lithium bis[oxalate-O,O'9 borate (LiBOB), lithium difluorobis[oxalate-O,O'] phosphate (LiPFO), and lithium tetrafluoro[oxalate-O,O'] phosphate. More preferably, the lithium salt is selected from one or more of $LiPF_6$, $LiBF_4$, $LiSO_3F$, lithium trifluoro((methylsulfonyl)oxy) borate (LiTFMSB), $LiPO_2F_2$, lithium bis[oxalate-O,O'] borate (LiBOB), and lithium difluorobis[oxalate-O,O'] phosphate (LiPFO). Even more preferably, the lithium salt is $LiPF_6$.

In the lithium-on battery of the present application, concentration of the lithium salt is not particularly limited, and may be adjusted according to actual needs.

In the lithium-ion battery in the present application, preferably, a conductivity of the electrolytic solution is 4 mS/cm~12 mS/cm at 25° C.

In the lithium-ion battery of the present application, a preparation method for the electrolytic solution is not limited, and the electrolytic solution may be prepared according to a method for a conventional electrolytic solution.

In the lithium-ion battery of the present application, $Li_{x1}Co_{y1}M_{1-y1}O_{2-z1}Q_{z1}$ may be specifically selected from one or more of $LiCo_{0.9}Zr_{0.1}O_2$, $LiCo_{0.9}Ti_{0.1}O_2$, $Li_{1.05}Co_{0.8}Mg_{0.2}O_2$, $Li_{1.01}Co_{0.98}Mg_{0.01}Ti_{0.005}Al_{0.005}O_2$, $Li_{1.05}Co_{0.98}Mg_{0.005}Zr_{0.005}Ti_{0.01}O_{1.9}F_{0.1}$, $Li_{1.1}Co_{0.95}Mg_{0.01}Zr_{0.01}Al_{0.03}O_2$, $Li_{1.04}Co_{0.95}Mg_{0.02}Zr_{0.03}O_{1.95}F_{0.05}$, $Li_{1.06}Co_{0.96}Mg_{0.02}Ti_{0.02}O_2$, $Li_{1.08}Co_{0.97}Mg_{0.01}Zr_{0.01}Al_{0.01}O_{1.9}S_{0.1}$, $Li_{1.09}Co_{0.98}Mg_{0.01}Ti_{0.005}Al_{0.005}O_2$, $Li_{1.085}Co_{0.98}Zr_{0.01}Ti_{0.005}Al_{0.005}O_{1.9}Cl_{0.1}$, $Li_{1.03}Co_{0.96}Mg_{0.01}Zr_{0.01}Ti_{0.01}Al_{0.01}O_2$, $Li_{1.04}Co_{0.97}Zr_{0.01}Al_{0.02}O_{1.9}F_{0.1}$, $Li_{1.07}Co_{0.97}Zr_{0.01}Ti_{0.01}Al_{0.01}O_{1.9}S_{0.1}$, $Li_{1.02}Co_{0.96}Mg_{0.02}Zr_{0.015}Ti_{0.005}O_{1.9}S_{0.1}$, $Li_{1.03}Co_{0.98}Ti_{0.01}Al_{0.01}O_{1.9}Cl_{0.1}$, $Li_{1.05}Co_{0.97}Mg_{0.01}Zr_{0.01}Al_{0.01}O_{1.9}Cl_{0.1}$, $Li_{1.04}Co_{0.95}Zr_{0.02}Ti_{0.03}O_{1.9}F_{0.1}$, $Li_{1.09}Co_{0.97}Mg_{0.02}Ti_{0.01}O_{1.95}F_{0.05}$, $Li_{1.03}Co_{0.95}Mg_{0.03}Ti_{0.02}O_{1.9}S_{0.1}$, and $Li_{1.04}Co_{0.97}Zr_{0.01}Ti_{0.01}Al_{0.01}O_{1.9}S_{0.1}$.

In the lithium-ion battery of the present application, the positive active material may further include one or more of lithium nickel oxide, a lithium manganese oxide, a lithium nickel manganese oxide, a lithium nickel cobalt manganese oxide, a lithium nickel cobalt aluminum oxide, and a compound obtained by adding another transition metal or non-transition metal to any of the foregoing oxide.

In the lithium-ion battery of the present application, a negative active material in the negative electrode sheet may be soft carbon, hard carbon, artificial graphite, natural graphite, silicon, silicon oxide compound, silicon carbon composite, lithium titanate, a metal that can form an alloy with lithium, or the like. One type of these negative active materials may be used individually, or two or more types of these negative active materials may be used in combination.

In the lithium-ion battery of the present application, the positive electrode sheet further includes a binder and a conductive agent. A positive slurry including the positive active material, the binder, and the conductive agent is applied onto a positive current collector, and then dried to give the positive electrode sheet. Types and amounts of the conductive agent and the binder are not specifically limited, and may be selected according to actual needs. A type of the positive current collector is not specifically limited either, and may be selected according to actual needs. Preferably, the positive current collector may be an aluminum foil.

Likewise, the negative electrode sheet further includes a binder and a conductive agent. A negative slurry containing the negative active material, the binder, and the conductive agent is applied onto a negative current collector, and then dried to give the negative electrode sheet. Types and amounts of the conductive agent and the binder are not specifically limited, and may be selected according to actual needs. A type of the negative current collector is not specifically limited either, and may be selected according to actual needs. Preferably, the negative current collector may be a copper foil.

In the lithium-ion battery of the present application, the separation film is disposed between the positive electrode sheet and the negative electrode sheet to have an effect of separation. A type of the separation film is not specifically limited, and the separation film may be, but not limited to, any separation film materials used in existing lithium-ion batteries, for example, polyethylene, polypropylene, polyvinylidene fluoride, and a multilayer composite film thereof.

In the lithium-ion battery of the present application, an end-of-charge voltage of the lithium-ion battery is not less than 4.2 V, that is, the lithium-ion battery may be used at a high voltage of not less than 4.2 V. Preferably, the end-of-charge voltage of the lithium-ion battery is not less than 4.35 V.

The lithium-ion battery of the present application may be either a hard-shell lithium-ion battery or a soft-package lithium-ion battery. Preferably, a metal hard shell is used for the hard-shell lithium-ion battery. Preferably, a packaging bag is used as a battery housing of the soft-package lithium-ion battery. The packaging bag typically includes an accommodating portion and a sealing portion. The accommodating portion is configured to accommodate the electrode assembly and the electrolytic solution, and the sealing portion is configured to seal the electrode assembly and the electrolytic solution.

The present application achieves more significant improvement on performance of the soft-package lithium-ion battery, because the soft-package lithium-ion battery is prone to swelling during use, whereas the present application could greatly reduce gas production of the battery and prevent from shortening the life of the battery due to the swelling of the soft-package lithium-ion battery.

In the lithium-ion battery of the present application, in the compounds represented by the Formula I-1, the Formula I-2, and the Formula I-3:

The $C_1$-$C_{12}$ alkyl group may be a chain alkyl group or a cyclic alkyl group, and the chain alkyl group may be a linear alkyl group or a branched chain alkyl group. Hydrogen on a ring of the cyclic alkyl group may be further replaced by an alkyl group. A preferred lower limit of the quantity of carbon atoms in the $C_1$-$C_{12}$ alkyl group is 1, 2, 3, 4, or 5, and a preferred upper limit is 3, 4, 5, 6, 8, 10, or 12. Preferably, a $C_1$-$C_{10}$ alkyl group is selected. More preferably, a $C_1$-$C_6$ chain alkyl group or a $C_3$-$C_8$ cyclic alkyl group is selected. Furthermore preferably, a $C_1$-$C_4$ chain alkyl group or a $C_5$-$C_7$ cyclic alkyl group is selected. Examples of the $C_1$-$C_{12}$ alkyl group may specifically include a methyl group, an ethyl group, an n-propyl group, isopropyl group, an n-butyl group, an isobutyl group, a sec-butyl group, a tert-butyl group, an n-pentyl group, an isopentyl group, a neopentyl group, a hexyl group, a 2-methyl-pentyl group, a 3-methyl-pentyl group, a 1,1,2-trimethyl-propyl group, a 3,3-dimethyl-butyl group, a heptyl group, a 2-heptyl group, a 3-heptyl group, a 2-methylhexyl group, a 3-methylhexyl group, an isoheptyl group, an octyl group, a nonyl group, and a decyl group.

When the aforementioned $C_1$-$C_{12}$ alkyl group contains oxygen atoms, the $C_1$-$C_{12}$ alkyl group may be a $C_1$-$C_{12}$ alkoxy group. Preferably, a $C_1$-$C_{10}$ alkoxy group is selected. More preferably, a $C_1$-$C_6$ alkoxy group is selected. Furthermore preferably, a $C_1$-$C_4$ alkoxy group is selected. Examples of the $C_1$-$C_{12}$ alkoxy group may specifically include a methoxy group, an ethoxy group, an n-propoxy group, an isopropoxy group, an n-butoxy group, a sec-butoxy group, a t-butoxy group, an n-pentyloxy group, an isopentyloxy group, a cyclopentyloxy group, and a cyclohexyloxy group.

The $C_2$-$C_{12}$ alkenyl group may be a cyclic alkenyl group or a chain alkenyl group, and the chain alkenyl group may be a linear alkenyl group or a branched alkenyl group. In addition, preferably, the $C_2$-$C_{12}$ alkenyl group has one double bond. A preferred lower limit of the quantity of carbon atoms in the $C_2$-$C_{12}$ alkenyl group is 2, 3, 4, or 5, and a preferred upper limit is 3, 4, 5, 6, 8, 10, or 12. Preferably, a $C_2$-$C_{10}$ alkenyl group is selected. More preferably, a $C_2$-$C_6$ alkenyl group is selected. Furthermore preferably, a $C_2$-$C_5$ alkenyl group is selected. Examples of the $C_2$-$C_{12}$ alkenyl group may specifically include a vinyl group, an allyl group, an isopropenyl group, a pentenyl group, a cyclohexenyl group, a cycloheptenyl group, and a cyclooctenyl group.

The $C_2$-$C_{12}$ alkynyl group may be a cyclic alkynyl group or a chain alkynyl group, and the chain alkynyl group may be a linear alkynyl group or a branched alkynyl group. In addition, preferably, the $C_2$-$C_{12}$ alkynyl group has one triple bond. A preferred lower limit of the quantity of carbon atoms in the $C_2$-$C_{12}$ alkynyl group is 2, 3, 4, or 5, and a preferred upper limit is 3, 4, 5, 6, 8, 10, or 12. Preferably, a $C_2$-$C_{10}$ alkynyl group is selected. More preferably, a $C_2$-$C_6$ alkynyl group is selected. Furthermore preferably, a $C_2$-$C_5$ alkynyl group is selected. Examples of the $C_2$-$C_{12}$ alkynyl group may specifically include an ethynyl group, a propargyl group, an isopropynyl group, a pentynyl group, a cyclohexynyl group, a cycloheptynyl group, and a cyclooctynyl group.

The $C_1$-$C_{12}$ amine group may be selected from

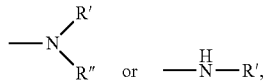

where R' and R" are selected from $C_1$-$C_{12}$ alkyl group.

The $C_6$-$C_{26}$ aryl group may be a phenyl group, a phenylalkyl group, a biphenyl group, or a fused ring aromatic hydrocarbon group (for example, a naphthyl group, an anthryl group, or a phenanthrenyl group). The biphenyl group and the fused ring aromatic hydrocarbon group may be further substituted with an alkyl group or an alkenyl group. Preferably, a $C_6$-$C_{16}$ aryl group is selected. More preferably, a $C_6$-$C_{14}$ aryl group is selected. Furthermore preferably, a $C_6$-$C_9$ aryl group is selected. Examples of the $C_6$-$C_{26}$ aryl group may specifically include a phenyl group, a benzyl group, a biphenyl group, a p-tolyl group, an o-tolyl group, an m-tolyl group, a naphthyl group, an anthryl group, and a phenanthryl group.

A hetero atom in the $C_2$-$C_{12}$ heterocyclic group may be selected from one or more of oxygen, nitrogen, sulfur, phosphorus, and boron, and a heterocyclic ring may be an aliphatic heterocyclic ring or an aromatic heterocyclic ring. Preferably, a $C_2$-$C_{10}$ heterocyclic group is selected. More preferably, a $C_2$-$C_7$ heterocyclic group is selected. Furthermore preferably, a five-membered aromatic heterocyclic ring, a six-membered aromatic heterocyclic ring, and a benzo heterocyclic ring are selected. Examples of the $C_2$-$C_{12}$ heterocyclic group may specifically include an ethylene oxide group, a propylene oxide group, an ethylene sulfide group, an aziridine group, a β-propiolactone group, a furyl group, a thienyl group, a pyrrolyl group, a thiazolyl group, an imidazolyl group, a pyridyl group, a pyrazinyl group, a pyrimidinyl group, a pyridazinyl group, an indolyl group, and a quinolinyl group.

The halogen atom used as a substituent group may be selected from one or more of a fluorine atom, a chlorine atom, and a bromine atom. Preferably, the halogen atom is a fluorine atom.

(1) Specifically, the compound represented by the Formula I-1 is a polynitrile pyrimidine compound.

In the Formula I-1:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, m is selected from 1 or 2.

Preferably, n is selected from 1 or 2.

Preferably, $R_1$, $R_3$ are the same group. More preferably, $R_1$, $R_3$, and $R_4$ are all the same group.

Preferably, $R_1$ and $R_3$ are both a hydrogen atom. More preferably, $R_1$, $R_3$, and $R_4$ are all a hydrogen atom.

Preferably, $R_1$, $R_2$, $R_3$, and $R_4$ are all a hydrogen atom; or $R_1$, $R_3$, and $R_4$ are all a hydrogen atom, and $R_2$ is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-1 may be specifically selected from one or more of the following compounds, but the present application is not limited thereto:

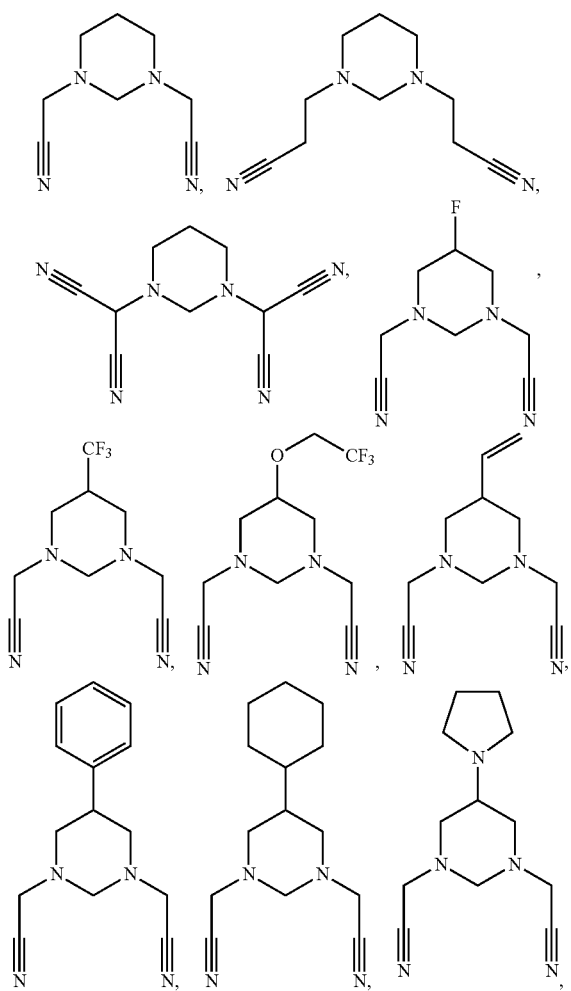

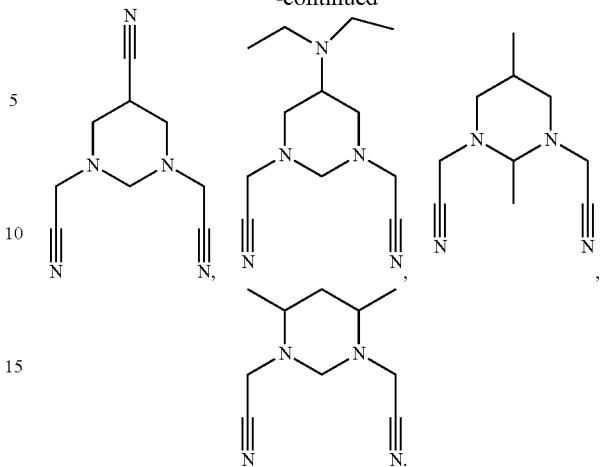

(2) Specifically, compounds represented by Formula I-2 are multi-cyano piperazine compounds.

In Formula I-2:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, m is selected from 1 or 2.

Preferably, n is selected from 1 or 2.

Preferably, at least two of $R_1$, $R_2$, $R_3$, and $R_4$ are the same group. More preferably, at least three of $R_1$, $R_2$, $R_3$, and $R_4$ are the same group.

Preferably, at least two of $R_1$, $R_2$, $R_3$, and $R_4$ are a hydrogen atom. More preferably, at least three of $R_1$, $R_2$, $R_3$, and $R_4$ are a hydrogen atom.

Preferably, $R_1$, $R_2$, $R_3$, and $R_4$ are all a hydrogen atom; or three of $R_1$, $R_2$, $R_3$, and $R_4$ are all a hydrogen atom, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-2 may be specifically selected from one or more of the following compounds, but the present application is not limited thereto:

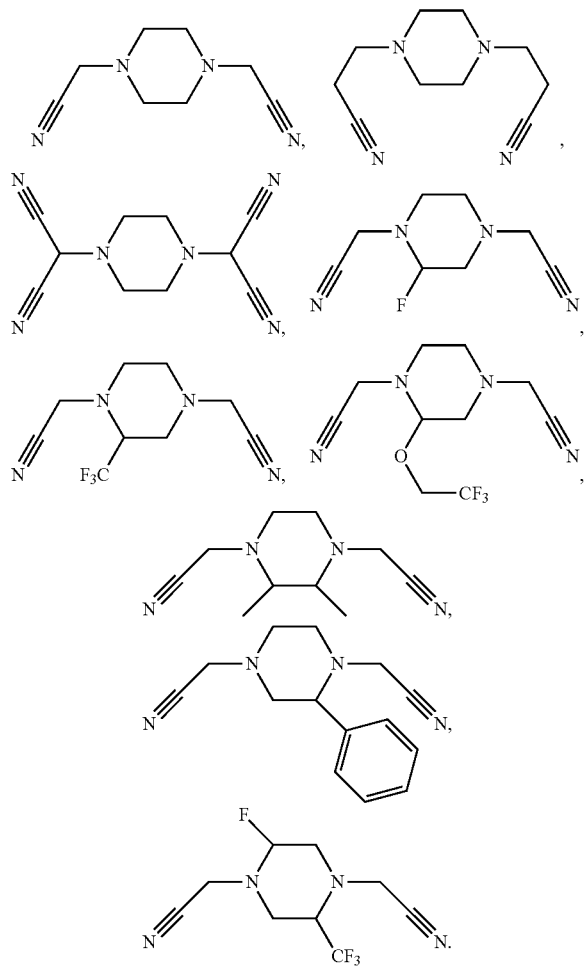

(3) Specifically, the compound represented by the Formula I-3 is a polynitrile s-triazine compound.

In the Formula I-3:

Preferably, $R_1$, $R_2$, and $R_3$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, and $R_3$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, z is selected from integers 0-6; more preferably, is selected from integers 0-4; furthermore preferably, is selected from 0, 1, or 2.

Preferably, m is selected from 1 or 2.

Preferably, n is selected from 1 or 2.

Preferably, k is selected from 1 or 2.

Preferably, at least two of $R_1$, $R_2$, and $R_3$ are the same group.

Preferably, at least two of $R_1$, $R_2$, and $R_3$ are a hydrogen atom.

Preferably, $R_1$, $R_2$, and $R_3$ are all a hydrogen atom; or two of $R_1$, $R_2$, and $R_3$ are a hydrogen atom, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-3 may be specifically selected from one or more of the following compounds, but the present application is not limited thereto:

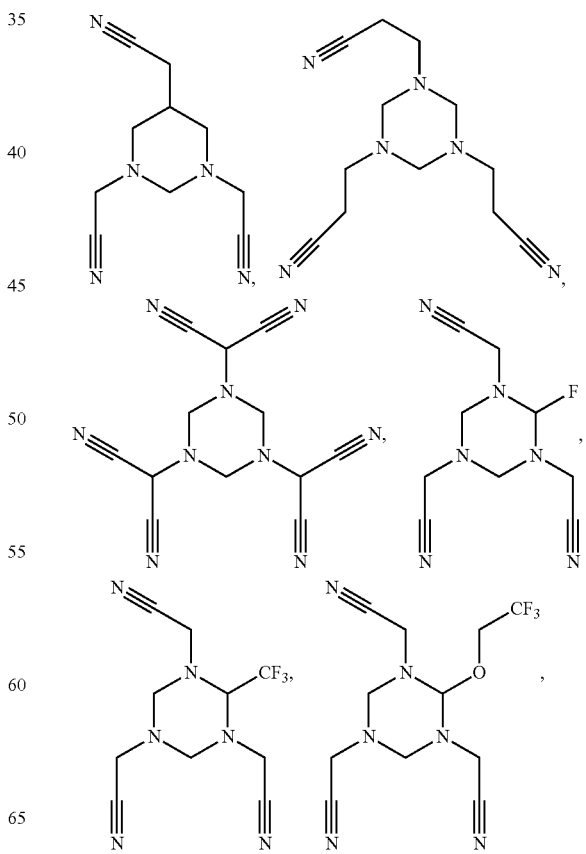

-continued

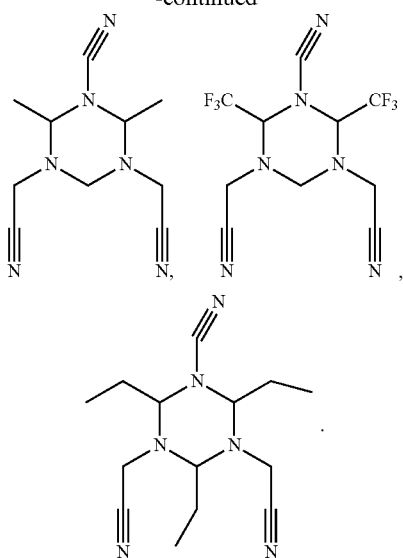

In the lithium-ion battery of the present application, the additive A may be synthesized by using the following method.

(1) Preparation of the Compound Represented by the Formula I-1

A reaction scheme is as follows:

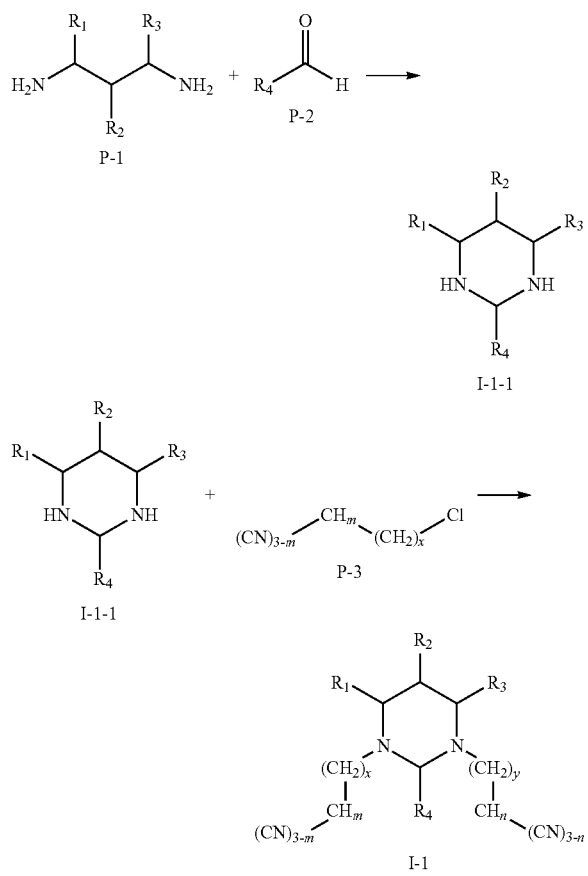

The specific preparation process is:

Adding aqueous solution P-2 with a concentration of 30%-40% dropwise to a raw material P-1 within 20 min-60 min, with quickly stirring the solution. After the dropwise addition is completed, quickly stirring the solution for 15 h-30 h. Stirring the solution in an oil bath at 70° C.-90° C. under reflux for 3 h-5 h to obtain a colorless, fuming, and viscous liquid intermediate product I-1-1. Then adding $K_2CO_3$, KI, and anhydrous acetonitrile, and quickly stirring them to form a solid-liquid mixture. Quickly adding a raw material P-3 at 40° C.-60° C., then stirring them for 10 h-20 h, and cooling the mixture to room temperature. Then performing separation and purification to obtain the compound represented by the Formula I-1.

(2) Preparation of the Compound Represented by the Formula I-2

A reaction scheme is as follows:

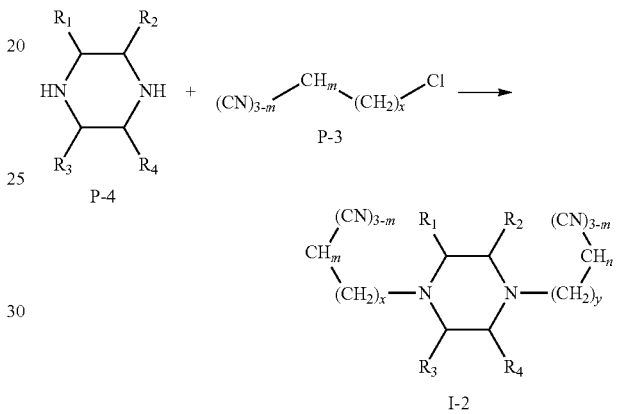

A specific preparation process includes the following steps:

Mixing anhydrous sodium carbonate, a raw material P-4 and a raw material P-3 in absolute ethanol, and stirring to react for 2 h~5 h; repeatedly washing with hot ethanol to obtain a crude product, and recrystallizing to obtain a compound represented by Formula I-2.

(3) Preparation of Compounds Represented by Formula I-3

The reaction equation is:

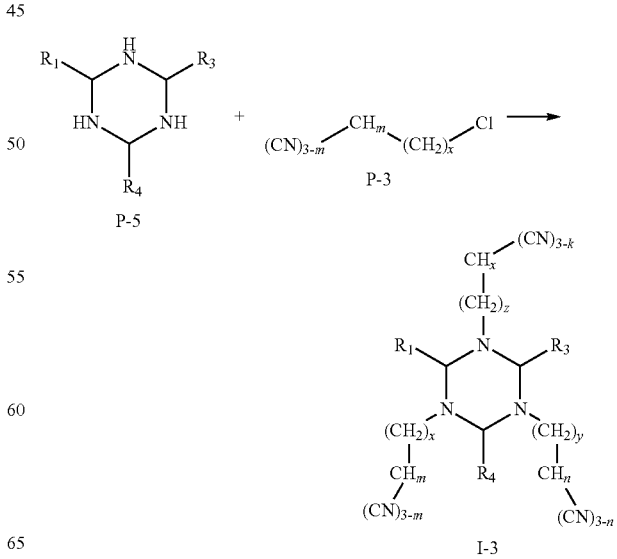

The specific preparation process is:

Mixing anhydrous sodium carbonate, a raw material P-5, and a raw material P-3 in absolute ethanol, and stirring them for 2 h-5 h for a reaction. Repeatedly washing with hot ethanol for a plurality of times to obtain a crude product, and performing recrystallization to obtain the compound represented by the Formula I-3.

In some embodiments, the lithium-ion battery may include an outer package for encapsulating the positive electrode sheet, the electrode sheet, and an electrolyte. In an example, the positive electrode sheet, the negative electrode sheet, and the separation film may be laminated or wound to form an electrode assembly of a laminated structure or an electrode assembly of a wound structure, and the electrode assembly is encapsulated in an outer package. The electrolyte may be an electrolytic solution, which infiltrates in the electrode assembly. There may be one or more electrode assemblies in the lithium-ion battery, depending on needs.

In some embodiments, the outer package of the lithium-ion battery may be a soft package, for example, a soft bag. A material of the soft package may be plastic, for example, may include one or more of polypropylene PP, polybutylene terephthalate PBT, polybutylene succinate PBS, and the like. Alternatively, the outer package of the lithium-ion battery may be a hard shell, for example, an aluminum shell.

Figure 4:
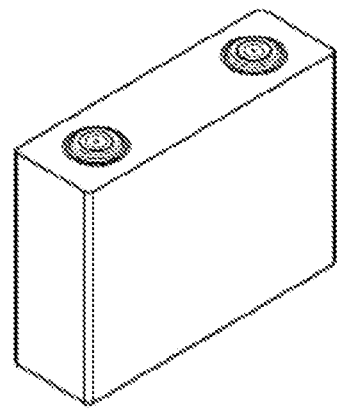
FIG. 4 is a schematic diagram of an embodiment of a lithium-ion battery.

Shape of the lithium-ion battery in the present application is not particularly limited, and may be of a cylindrical, square, or any other shape. FIG. 4 shows an example of a lithium-ion battery 5 of a square structure.

In some embodiments, lithium-ion batteries may be assembled into a battery module, and the battery module may include a plurality of lithium-ion batteries. A specific quantity may be adjusted based on application and capacity of the battery module.

Figure 5:
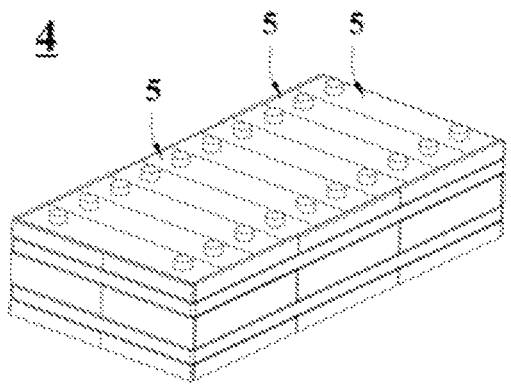
FIG. 5 is a schematic diagram of an embodiment of a battery module.

FIG. 5 shows an example of a battery module 4. Referring to FIG. 5, in the battery module 4, a plurality of lithium-ion batteries 5 may be sequentially arranged along a length direction of the battery module 4; or certainly, may be arranged in any other manner. Further, the plurality of lithium-ion batteries 5 may be fixed by using fasteners.

Optionally, the battery module 4 may further include a housing with an accommodating space, and the plurality of lithium-ion batteries 5 are accommodated in the accommodating space.

In some embodiments, battery modules may be further assembled into a battery pack, and the quantity of battery modules included in the battery pack may be adjusted based on application and capacity of the battery pack.

Figure 6:
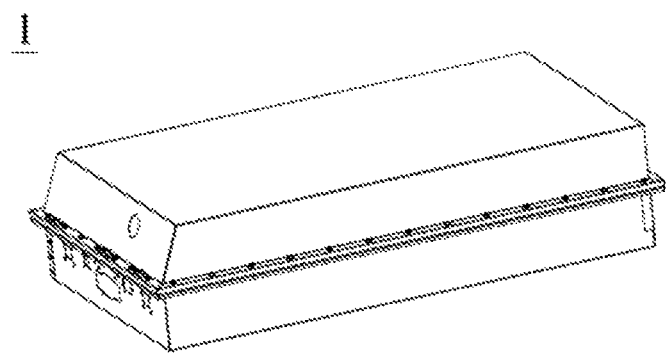
FIG. 6 is a schematic diagram of an embodiment of a battery pack.
Figure 7:
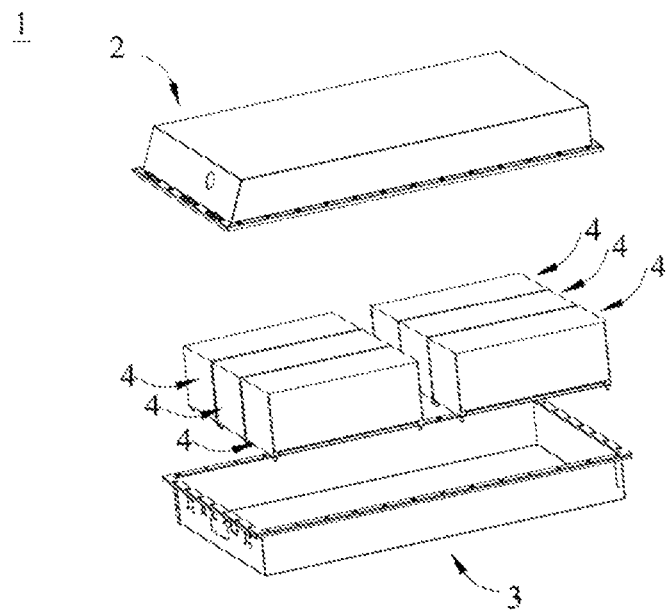
FIG. 7 is an exploded diagram of FIG. 6.

FIG. 6 and FIG. 7 show an example of a battery pack 1. Referring to FIG. 6 and FIG. 7, the battery pack 1 may include a battery cabinet and a plurality of battery modules 4 disposed in the battery cabinet. The battery cabinet includes an upper cabinet body 2 and a lower cabinet body 3. The upper cabinet body 2 can cover the cabinet body 3 and form an enclosed space for accommodating the battery modules 4. The plurality of battery modules 4 may be arranged in the battery cabinet in any manner.

An apparatus according to a second aspect of the present application is described next.

A second aspect of the present application provides an apparatus. The apparatus includes the lithium-ion battery in the first aspect of the present application, and the lithium-ion battery supplies power to the apparatus. The apparatus may be, but not limited to, a mobile device (for example, a mobile phone or a notebook computer), an electric vehicle (for example, a full electric vehicle, a hybrid electric vehicle, a plug-in hybrid electric vehicle, an electric bicycle, an electric scooter, an electric golf vehicle, or an electric truck), an electric train, a ship, a satellite, an energy storage system, and the like.

A lithium-ion battery, a battery module, or a battery pack may be selected for the apparatus according to requirements for using the apparatus.

Figure 8:
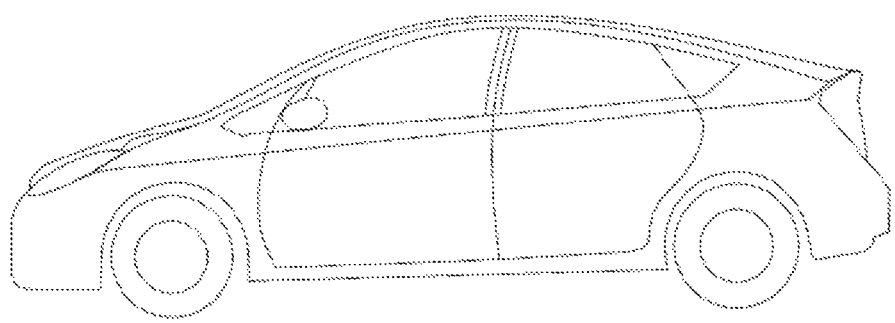
FIG. 8 is a schematic diagram of an embodiment of an apparatus using a lithium-ion battery as a power source.

FIG. 8 shows an example of an apparatus. The apparatus is a full electric vehicle, a hybrid electric vehicle, a plug-in hybrid electric vehicle, or the like. To meet a requirement of the apparatus for high power and a high energy density of a lithium-ion battery, a battery pack or a battery module may be used.

In another example, the apparatus may be a mobile phone, a tablet computer, a notebook computer, or the like. The apparatus is generally required to be light and thin, and may use a lithium-ion battery as its power source.

To make the objectives, technical solutions, and beneficial technical effects of the present application clearer, the present application is further described below in detail with reference to embodiments. It should be understood that the embodiments described in this specification are merely intended to explain the present application, but not to limit the present application. Formulations, proportions, and the like of the embodiments may be adjusted according to local conditions without substantial effect on results.

All reagents, materials, and instruments that are used in Examples and Comparative Examples are commercially available unless otherwise specified. Specific synthesis processes of additives A1, A2, and A3 are as follows. Other types of additives A may be synthesized according to similar methods.

Synthesis of the Additive A1:

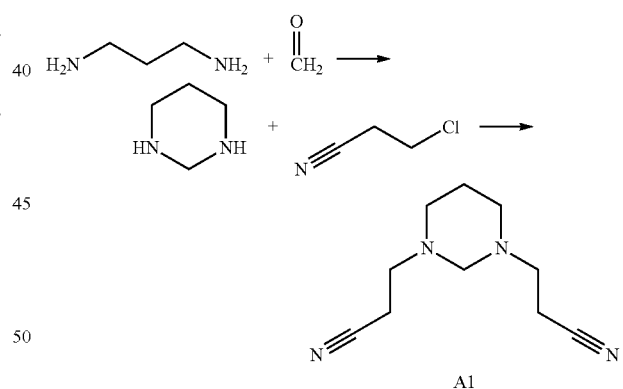

A1

37% formaldehyde aqueous solution was added dropwise to 1,3-propanediamine within 0.5 h with quick stirring. After the completion of dropwise addition, the solution was still quickly stirred for 20 h. Then the solution was stirred in an oil bath at 80° C. reflux for 4 h to obtain intermediate product hexahydropyrimidine as a colorless, fuming, and viscous liquid. $K_2CO_3$, KI, and anhydrous acetonitrile were added, followed by quick stirring to form a solid-liquid mixture. Then β-chloropropionitrile was added at 60° C. within 0.5 h. The mixture was stirred for 17 h, and cooled to room temperature. Then the mixture was subjected to separation and purification to obtain A1. Carbon nuclear magnetic resonance spectroscopy was shown in FIG. 1.

Synthesis of the Additive A2:

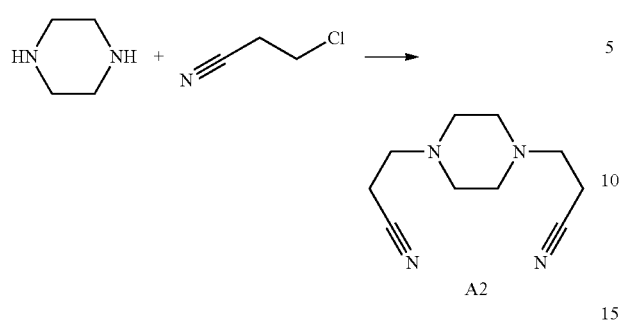

Figure 2:
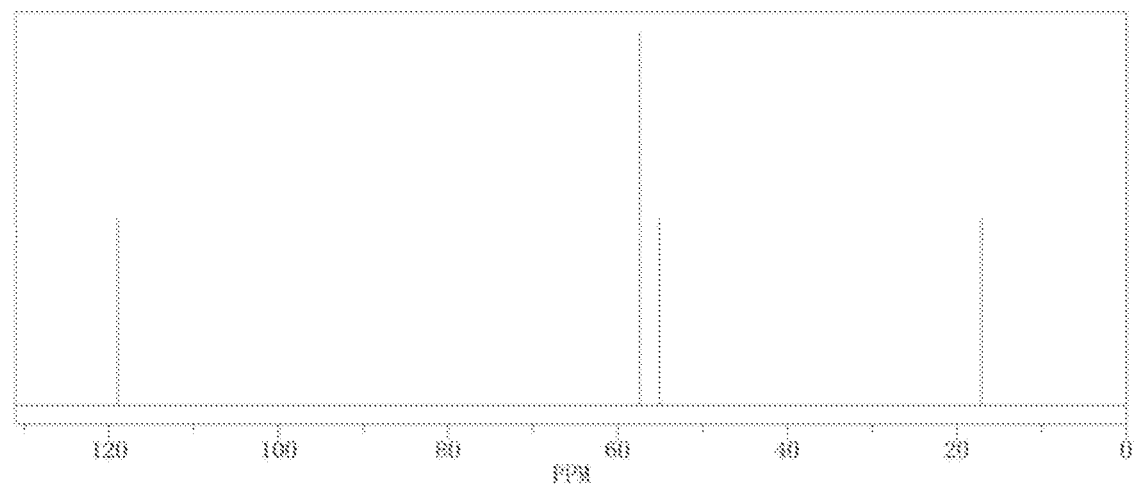
FIG. 2 is a carbon nuclear magnetic resonance spectrum of a compound A2.

Anhydrous sodium carbonate, piperazine, and β-chloropropionitrile were mixed in absolute ethanol, and stirred for 4 h for reaction. The mixture was repeatedly washed with hot ethanol for a plurality of times to obtain a crude product, and subjected to recrystallization to obtain A2. Carbon nuclear magnetic resonance spectroscopy was shown in FIG. 2.

Synthesis of the Additive A3:

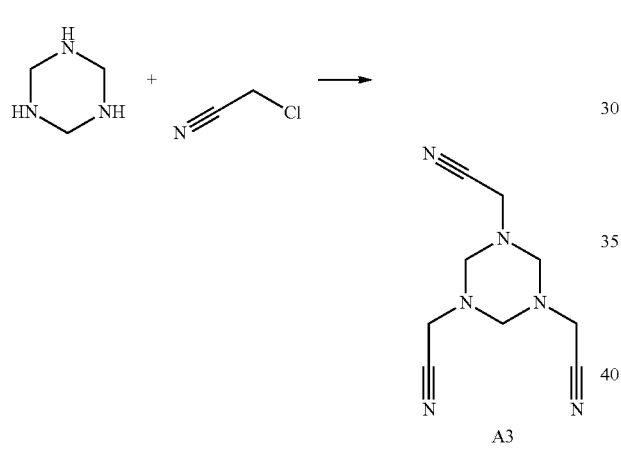

Figure 3:
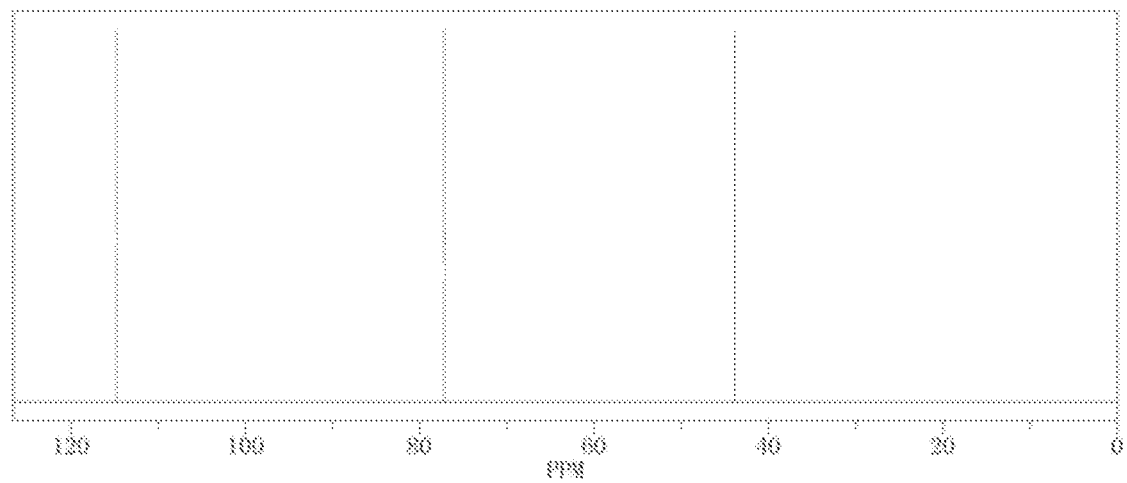
FIG. 3 is a carbon nuclear magnetic resonance spectrum of a compound A3.

Anhydrous sodium carbonate, 1,3,5-s-triazine, and chloroacetonitrile were mixed in absolute ethanol, and stirred for 4 h for reaction. The mixture was repeatedly washed with hot ethanol for a plurality of times to obtain a crude product, and subjected to recrystallization to obtain A3. Carbon nuclear magnetic resonance spectroscopy was shown in FIG. 3.

In Examples 1-30 and reference Comparative Examples 1-2, lithium-ion batteries was prepared according to the following method.

(1) Preparation of an Electrolytic Solution

A mixed solution of ethylene carbonate (EC for short), ethyl methyl carbonate (EMC for short) and diethyl carbonate (DEC for short) was used as an organic solvent, where a mass ratio of EC, EMC, and DEC was 1:1:1. $LiPF_6$ was used as a lithium salt in an amount of 12.5% relative to the total mass of the electrolytic solution. Additives were added according to electrolytic solution composition as shown in Table 1, where percents of all additive components are calculated relative to the total mass of the electrolytic solution.

Additives A used in the Examples and Comparative Examples were abbreviated as follows:

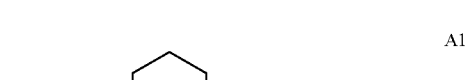
A1

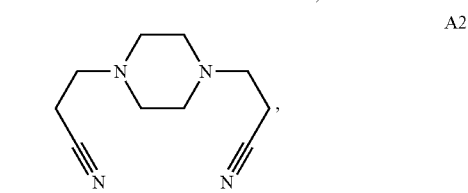
A2

A3

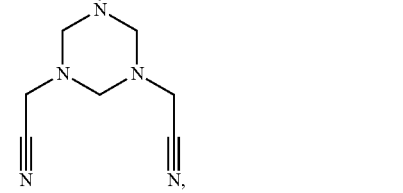
A4

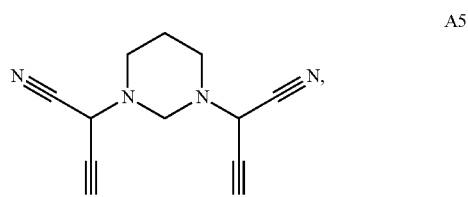
A5

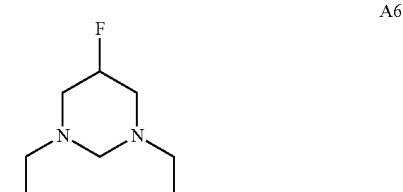
A6

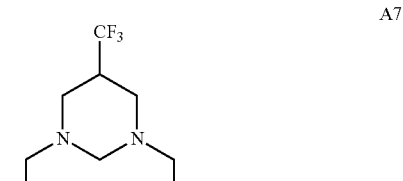
A7

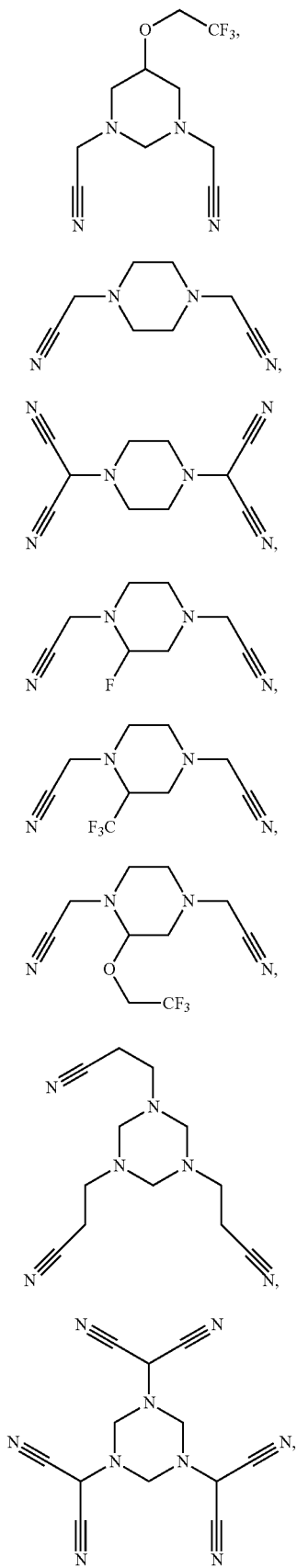

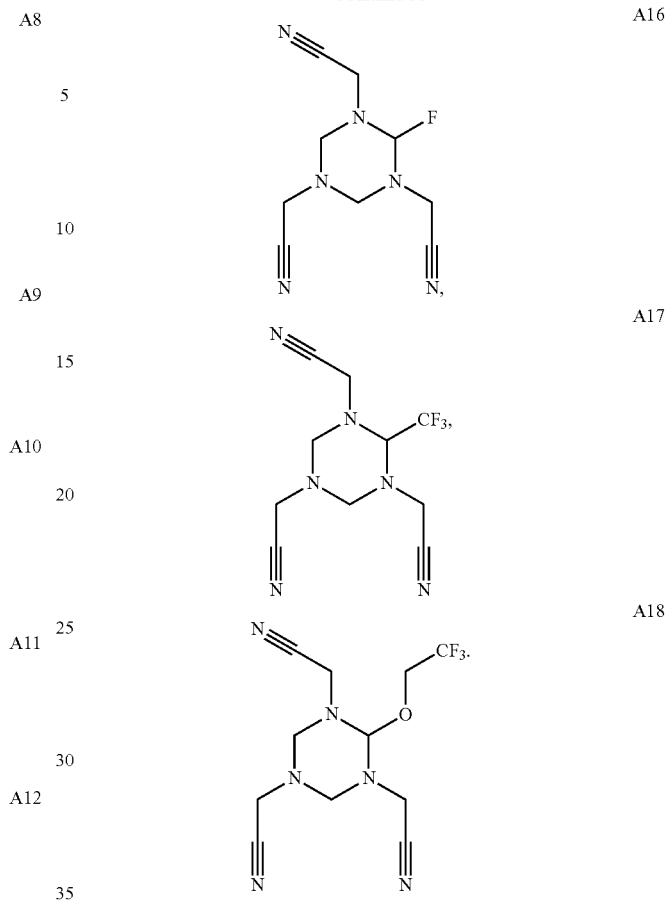

(2) Preparation of a Positive Electrode Sheet

A positive active material, a binder polyvinylidene fluoride (PVDF), and a conductive agent acetylene black in Table 1 based on a mass ratio of 98:1:1 were mixed. N-methylpyrrolidone was added. The resulting mixture was stirred by using a vacuum mixer until the mixture was stable and uniform, to obtain a positive slurry. The positive slurry was uniformly applied onto an aluminum foil. The aluminum foil was dried at room temperature, and transferred to a blast oven at 120° C. for 1 h. Then the aluminum foil was cold-pressed and cut to obtain a positive electrode sheet.

(3) Preparation of a Negative Electrode Sheet

A negative active material graphite, a conductive agent acetylene black, a thickening agent sodium carboxymethyl cellulose, and a binder styrene-butadiene rubber based on a mass ratio of 97:1:1:1 were mixed. Deionized water was added. The resulting mixture was stirred by using a vacuum mixer until the mixture was stable and uniform, to obtain a negative slurry. The negative slurry was uniformly applied onto a copper foil. The copper foil was dried at room temperature, and transferred to a blast oven at 120° C. for 1 h. Then the copper foil was cold-pressed and cut to obtain a negative electrode sheet.

(4) Preparation of a Lithium-Ion Battery

The positive electrode sheet, the negative electrode sheet, and a polypropylene (PP)/polyethylene (PE)/PP separation film were wound to obtain an electrode assembly. The electrode assembly was placed into an aluminum-plastic film of a packaging bag, followed by injection of the electrolytic solution. Then a procedure including sealing, standing, hot-pressing and cold-pressing, forming, gas exhausting, and capacity testing were performed to obtain a lithium-ion battery.

TABLE 1

Parameters of Examples 1-30 and Comparative Examples 1-2

| | Positive active material | Amount of VC | Amount of FEC | Amount of PS | Additive A Type | Additive A Amount |
|---|---|---|---|---|---|---|
| Example 1 | $Li_{1.05}Co_{0.98}Mg_{0.005}Zr_{0.005}Ti_{0.01}O_{1.9}F_{0.1}$ | 2.00% | 4.00% | 3.00% | A1 | 0.10% |
| Example 2 | $Li_{1.05}Co_{0.98}Mg_{0.005}Zr_{0.005}Ti_{0.01}O_{1.9}F_{0.1}$ | 2.00% | 4.00% | 3.00% | A1 | 1.00% |
| Example 3 | $Li_{1.05}Co_{0.98}Mg_{0.005}Zr_{0.005}Ti_{0.01}O_{1.9}F_{0.1}$ | 2.00% | 4.00% | 3.00% | A1 | 2.00% |
| Example 4 | $Li_{1.05}Co_{0.98}Mg_{0.005}Zr_{0.005}Ti_{0.01}O_{1.9}F_{0.1}$ | 2.00% | 4.00% | 3.00% | A1 | 3.50% |
| Example 5 | $Li_{1.05}Co_{0.98}Mg_{0.005}Zr_{0.005}Ti_{0.01}O_{1.9}F_{0.1}$ | 2.00% | 4.00% | 3.00% | A1 | 6.00% |
| Example 6 | $Li_{1.05}Co_{0.98}Mg_{0.005}Zr_{0.005}Ti_{0.01}O_{1.9}F_{0.1}$ | 2.00% | 4.00% | 3.00% | A1 | 8.00% |
| Example 7 | $Li_{1.05}Co_{0.98}Mg_{0.005}Zr_{0.005}Ti_{0.01}O_{1.9}F_{0.1}$ | 2.00% | 4.00% | 3.00% | A1 | 10.00% |
| Example 8 | $Li_{1.05}Co_{0.98}Mg_{0.005}Zr_{0.005}Ti_{0.01}O_{1.9}F_{0.1}$ | 0.10% | 4.00% | 3.00% | A1 | 2.00% |
| Example 9 | $Li_{1.05}Co_{0.98}Mg_{0.005}Zr_{0.005}Ti_{0.01}O_{1.9}F_{0.1}$ | 10.00% | 4.00% | 3.00% | A1 | 2.00% |
| Example 10 | $Li_{1.05}Co_{0.98}Mg_{0.005}Zr_{0.005}Ti_{0.01}O_{1.9}F_{0.1}$ | 2.00% | 0.10% | 3.00% | A1 | 2.00% |
| Example 11 | $Li_{1.05}Co_{0.98}Mg_{0.005}Zr_{0.005}Ti_{0.01}O_{1.9}F_{0.1}$ | 2.00% | 10.00% | 3.00% | A1 | 2.00% |
| Example 12 | $Li_{1.05}Co_{0.98}Mg_{0.005}Zr_{0.005}Ti_{0.01}O_{1.9}F_{0.1}$ | 2.00% | 4.00% | 0.10% | A1 | 2.00% |
| Example 13 | $Li_{1.05}Co_{0.98}Mg_{0.005}Zr_{0.005}Ti_{0.01}O_{1.9}F_{0.1}$ | 2.00% | 4.00% | 10.00% | A1 | 2.00% |
| Example 14 | $Li_{1.01}Co_{0.98}Mg_{0.01}Ti_{0.005}Al_{0.005}O_2$ | 2.00% | 4.00% | 3.00% | A2 | 2.00% |
| Example 15 | $Li_{1.1}Co_{0.95}Mg_{0.01}Zr_{0.01}Al_{0.03}O_2$ | 2.00% | 4.00% | 3.00% | A3 | 2.00% |
| Example 16 | $Li_{1.04}Co_{0.95}Mg_{0.02}Zr_{0.03}O_{1.95}F_{0.05}$ | 2.00% | 4.00% | 3.00% | A4 | 2.00% |
| Example 17 | $Li_{1.08}Co_{0.97}Mg_{0.01}Zr_{0.01}Al_{0.01}O_{1.9}S_{0.1}$ | 2.00% | 4.00% | 3.00% | A5 | 2.00% |
| Example 18 | $Li_{1.085}Co_{0.98}Zr_{0.01}Ti_{0.005}Al_{0.005}O_{1.9}Cl_{0.1}$ | 2.00% | 4.00% | 3.00% | A6 | 2.00% |
| Example 19 | $Li_{1.03}Co_{0.96}Mg_{0.01}Zr_{0.01}Ti_{0.01}Al_{0.01}O_2$ | 2.00% | 4.00% | 3.00% | A7 | 2.00% |
| Example 20 | $Li_{1.06}Co_{0.96}Mg_{0.02}Ti_{0.02}O_2$ | 2.00% | 4.00% | 3.00% | A8 | 2.00% |
| Example 21 | $Li_{1.09}Co_{0.98}Mg_{0.01}Ti_{0.005}Al_{0.005}O_2$ | 2.00% | 4.00% | 3.00% | A9 | 2.00% |
| Example 22 | $Li_{1.04}Co_{0.97}Zr_{0.01}Al_{0.02}O_{1.9}F_{0.1}$ | 2.00% | 4.00% | 3.00% | A10 | 2.00% |
| Example 23 | $Li_{1.07}Co_{0.97}Zr_{0.01}Ti_{0.01}Al_{0.01}O_{1.9}S_{0.1}$ | 2.00% | 4.00% | 3.00% | A11 | 2.00% |
| Example 24 | $Li_{1.02}Co_{0.96}Mg_{0.02}Zr_{0.015}Ti_{0.005}O_{1.9}S_{0.1}$ | 2.00% | 4.00% | 3.00% | A12 | 2.00% |
| Example 25 | $Li_{1.03}Co_{0.98}Ti_{0.01}Al_{0.01}O_{1.9}Cl_{0.1}$ | 2.00% | 4.00% | 3.00% | A13 | 2.00% |
| Example 26 | $Li_{1.05}Co_{0.97}Mg_{0.01}Zr_{0.01}Al_{0.01}O_{1.9}Cl_{0.1}$ | 2.00% | 4.00% | 3.00% | A14 | 2.00% |
| Example 27 | $Li_{1.04}Co_{0.95}Zr_{0.02}Ti_{0.03}O_{1.9}F_{0.1}$ | 2.00% | 4.00% | 3.00% | A15 | 2.00% |
| Example 28 | $Li_{1.09}Co_{0.97}Mg_{0.02}Ti_{0.01}O_{1.95}F_{0.05}$ | 2.00% | 4.00% | 3.00% | A16 | 2.00% |
| Example 29 | $Li_{1.03}Co_{0.95}Mg_{0.03}Ti_{0.02}O_{1.9}S_{0.1}$ | 2.00% | 4.00% | 3.00% | A17 | 2.00% |
| Example 30 | $Li_{1.04}Co_{0.97}Zr_{0.01}Ti_{0.01}Al_{0.01}O_{1.9}S_{0.1}$ | 2.00% | 4.00% | 3.00% | A18 | 2.00% |
| Comparative Example 1 | $LiCoO_2$ | / | / | / | / | / |
| Comparative Example 2 | $Li_{1.05}Co_{0.98}Mg_{0.005}Zr_{0.005}Ti_{0.01}O_{1.9}F_{0.1}$ | 2.00% | 4.00% | 3.00% | adiponitrile | 2.00% |

Tests for lithium-ion battery are described below.

(1) Cycle Performance Test for a Lithium-Ion Battery at Normal Temperature and High Voltage At 25° C., the lithium-ion battery is charged at a constant current of 1 C until a voltage of 4.35 V is reached, further charged at a constant voltage of 4.35 V until a current of 0.05 C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine a discharge capacity at the 200th cycle.

Capacity retention rate (%) of a lithium-ion battery after 200 cycles=(the discharge capacity of the lithium-ion battery after 200 cycles/the discharge capacity of the lithium-ion battery at the first cycle)×100%.

(2) Cycle Performance Test for a Lithium-Ion Battery Under High-Temperature and High-Voltage Conditions At 45° C., the lithium-ion battery is charged at a constant current of 1 C until a voltage of 4.35 V is reached, further charged at a constant voltage of 4.35 V until a current of 0.05 C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine a discharge capacity at the $200^{th}$ cycle.

Capacity retention rate (%) of a lithium-ion battery after 200 cycles=(the discharge capacity of the lithium-ion battery after 200 cycles/the discharge capacity of the lithium-ion battery at the first cycle)×100%.

(3) Storage Performance Test for a Lithium-Ion Battery at High Temperature

At 25° C., the lithium-ion battery is charged at a constant current of 0.5 C until a voltage of 4.35 V is reached, and then charged at a constant voltage of 4.35 V until a current of 0.05 C is reached. The thickness of the lithium-ion battery is tested and denoted the thickness as $h_0$. Then the lithium-ion battery is placed in a constant-temperature box at 85° C., stored for 24 h, and then taken out. Then the thickness of the lithium-ion battery is tested again and denoted as $h_1$.

Thickness expansion rate (%) of a lithium-ion battery after storage at 85° C. for 24 h=$[(h_1-h_0)/h_0]\times 100\%$.

TABLE 2

Performance test results of Examples 1-30 and Comparative Examples 1-2

| | Capacity retention rate after 200 cycles at 25° C./4.35 V | Capacity retention rate after 200 cycles at 45° C./4.35 V | Thickness expansion rate at 85° C./24 h |
|---|---|---|---|
| Example 1 | 90% | 83% | 12% |
| Example 2 | 97% | 93% | 5% |

TABLE 2-continued

Performance test results of Examples 1-30 and Comparative Examples 1-2

|  | Capacity retention rate after 200 cycles at 25° C./4.35 V | Capacity retention rate after 200 cycles at 45° C./4.35 V | Thickness expansion rate at 85° C./24 h |
|---|---|---|---|
| Example 3 | 99% | 95% | 2% |
| Example 4 | 97% | 92% | 2% |
| Example 5 | 94% | 87% | 1% |
| Example 6 | 89% | 80% | 1% |
| Example 7 | 84% | 73% | 1% |
| Example 8 | 97% | 93% | 3% |
| Example 9 | 89% | 83% | 18% |
| Example 10 | 96% | 92% | 4% |
| Example 11 | 90% | 83% | 16% |
| Example 12 | 96% | 92% | 6% |
| Example 13 | 79% | 62% | 1% |
| Example 14 | 98% | 94% | 3% |
| Example 15 | 97% | 93% | 5% |
| Example 16 | 99% | 95% | 7% |
| Example 17 | 96% | 92% | 3% |
| Example 18 | 96% | 92% | 4% |
| Example 19 | 98% | 94% | 4% |
| Example 20 | 96% | 92% | 5% |
| Example 21 | 97% | 93% | 6% |
| Example 22 | 97% | 93% | 3% |
| Example 23 | 97% | 93% | 7% |
| Example 24 | 99% | 95% | 8% |
| Example 25 | 98% | 94% | 5% |
| Example 26 | 97% | 93% | 6% |
| Example 27 | 95% | 91% | 4% |
| Example 28 | 99% | 95% | 2% |
| Example 29 | 97% | 93% | 5% |
| Example 30 | 98% | 94% | 3% |
| Comparative Example 1 | 85% | 78% | 42% |
| Comparative Example 2 | 92% | 85% | 9% |

It can be seen from comparisons between Examples 1-30 and Comparative Examples 1-2 that the lithium-ion batteries of the present application have super cycle performance and storage performance under high-temperature and high-voltage conditions.

Compared with Comparative Example 1, in Examples of the present application, the metal ion M-doped lithium cobalt oxide material $Li_{x1}Co_{y1}M_{1-y1}O_{2-z1}Q_{z1}$ was used as the positive active material, and VC, FEC, PS, and an additive A were used as an electrolytic solution additive. The doping element M served as a framework in the positive active material. This reduced lattice deformation of the positive active material during deep delithiation, delayed degradation of bulk structure of the positive active material, and greatly improved structural stability of the lithium-ion battery when the lithium-ion battery was used at high voltage. The additive A was a polynitrile six-membered nitrogen-heterocyclic compound with a relatively low oxidation potential, such that a stable complex layer was formed on a surface of the positive active material during formation of the battery. This effectively passivated the surface of the positive active material, reduced surface activity of the positive active material, and avoided direct contact between the electrolytic solution and the surface of the positive active material, thereby greatly reducing surface side reactions, and correspondingly reducing lithium ions consumed in the side reactions, and thus greatly decreasing a consumption rate of reversible lithium ions. The actual effect finally manifested was that capacity retention rate of the lithium-ion battery after cycling was greatly increased. Due to the production gas in some surface side reactions, the reduction of surface side reactions further indicated a decrease in gas production of the battery. The actual effect finally manifested was that thickness expansion of the lithium-ion battery was significantly reduced at high temperature. VC, FEC, PS may form, on surfaces of positive and negative electrodes, a surface film containing double bonds, fluorine atoms, and sulfonate groups. The surface film had good chemical, electrochemical, mechanical, and thermal stability, and could avoid direct contact between the electrolytic solution and the surfaces of the positive and negative electrodes while smoothly conducting lithium ions, thereby providing an effect of suppressing oxidation and reduction side reaction on the surfaces of the positive and negative electrodes, so that the gas production of the battery could be significantly suppressed.

Compared with the linear nitrile compound used in Comparative Example 2, the polynitrile six-membered nitrogen-heterocyclic compound in Examples had a special six-membered nitrogen-heterocyclic structure with a spacing between nitrile groups closer to that between transition metals on the surface of the positive active material. This could maximize complexation of the nitrile groups and allow more nitrile groups to have a complexation effect. Therefore, the polynitrile six-membered nitrogen-heterocyclic compound in Examples had stronger coverage on a transition metal on the surface of the positive active material, better passivation on the surface of the positive active material, and also outstanding improvement on cycle performance and storage performance of the lithium-ion battery.

It can be further seen from Examples 1-7 that, when an end-of-charge voltage was fixed at 4.35 V, with an increase (from 0.1% to 10%) in the amount of the additive A, the capacity retention rate of the lithium-ion battery after cycling at 25° C. and 45° C. showed an ascent and then showed a decline trend, and the thickness expansion rate after storage at 85° C. for 24 h was decreasing. This was because when the amount of the additive A was relatively large, the complex layer formed by the additive A being adsorbed on the surface of the positive active material was likely to be thicker and denser, affecting diffusion and migration of lithium ions, and greatly increasing positive electrode impedance. Secondly, the additive A consumed lithium ions while forming the complex layer, reducing lithium ions available for cycling. Finally, a relatively large amount of the additive A caused an increase in overall viscosity of the electrolytic solution and a decrease in an ionic conductivity, so that the capacity retention rate of the lithium-ion battery after cycling at 25° C. and 45° C. showed an ascent and then showed a decline trend. Therefore, the amount of the additive A needs to be appropriate. Preferably, the amount is 0.1%-10%; more preferably, is 0.1%-6%; furthermore preferably, is 0.1%-3.5%.

It can be further seen from Examples 8-11 that when the amounts of VC and FEC were relatively large, the thickness expansion rate of the lithium-ion battery after storage at 85° C. for 24 h increased. This was because VC and FEC had poor thermal stability, and when the amounts of VC and FEC were relatively large, some VC and FEC could be decomposed, resulting in the increase of gas production of the battery. Therefore, the amounts of VC and FEC needs to be appropriate. Preferably, the amount is 0.1%-10%, and more preferably 0.1%-5%.

It can be further seen from Examples 12-13 that, when the amount of PS is relatively large, the cycle capacitance retention rate of the lithium-ion battery decreased at 25° C. and 45° C. This was because the surface film formed with the participation of PS is not long-lasting and the surface film would be continuously oxidized and decomposed during the cycle, and a thicker surface film was formed on surfaces of the positive and negative electrodes. This could greatly increase impedances of the positive and negative electrodes. Therefore, the cycle capacity retention rate of the lithium-ion battery could decreased at 25° C. and 45° C. Therefore, the amount of PS needs to be appropriate. Preferably, the amount is 0.1%-10%, and more preferably 0.1%-5%.

According to the disclosure and guidance in this specification, a person skilled in the art to which the present application relates may also make appropriate changes and modifications to the foregoing embodiments. Therefore, the present application is not limited to the specific embodiments disclosed and described above, and modifications and changes to the present application shall also fall within the protection scope of the claims of the present application. In addition, although some specific terms are used in this specification, these terms are merely intended for ease of description, and do not constitute any limitation on the present application.

What is claimed is:

1. A lithium-ion battery comprising an electrode assembly and an electrolytic solution, wherein the electrode assembly comprises a positive electrode sheet, a negative electrode sheet, and a separation film;
wherein
a positive active material in the positive electrode sheet comprises $Li_{x1}Co_{y1}M_{1-y1}O_{2-z1}Q_{z1}$, $0.5 \leq x1 \leq 1.2$, $0.8 \leq y1 \leq 1.0$, $0 \leq z1 \leq 0.1$, M is one or more selected from the group consisting of Al, Ti, Zr, Y, and Mg, and Q is one or more selected from the group consisting of F, Cl, and S;
the electrolytic solution contains vinylene carbonate, fluoroethylene carbonate, 1,3-propane sultone, and an additive A, wherein based on total mass of the electrolytic solution, a mass percentage of the additive A is 0.1%-10% and a mass percentage of each of the vinylene carbonate, the fluoroethylene carbonate, and the 1,3-propane sultone is 0.1%-10% respectively;
wherein, the additive A is one or more selected from the group consisting of compounds;

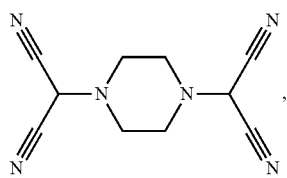

Formula I-2(3)

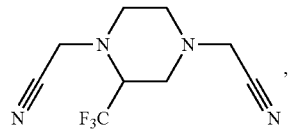

Formula I-2(5)

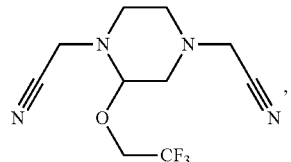

Formula I-2(6)

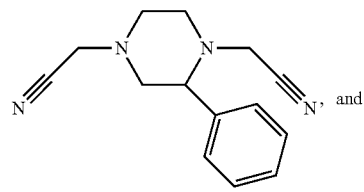

Formula I-2(8)

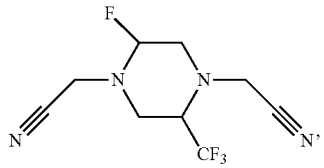

Formula I-2(9)

2. The lithium-ion battery according to claim 1, wherein, based on total mass of the electrolytic solution, a mass percentage of the additive A is 0.1%-3.5%.

3. The lithium-ion battery according to claim 1, wherein, based on total mass of the electrolytic solution, a mass percentage of each of the vinylene carbonate, the fluoroethylene carbonate, and the 1,3-propane sultone is 0.1%-5% respectively.

4. The lithium-ion battery according to claim 1, wherein an end-of-charge voltage of the lithium-ion battery is 4.2 V-4.35V.

5. The lithium-ion battery according to claim 1, wherein the lithium-ion battery is a hard-shell lithium-ion battery or a soft-package lithium-ion battery.

6. An apparatus, comprising the lithium-ion battery according to claim 1.

* * * * *